United States Patent
Ochi et al.

(10) Patent No.: US 7,632,813 B2
(45) Date of Patent: Dec. 15, 2009

(54) BONE DENSIFYING AGENT CHARACTERIZED BY USE OF CATHEPSIN K INHIBITOR WITH PTH

(75) Inventors: Yasuo Ochi, Mishima-gun (JP); Makoto Tanaka, Mishima-gun (JP); Naoki Kawada, Mishima-gun (JP); Hiroyuki Yamada, Mishima-gun (JP); Hiroshi Mori, Mishima-gun (JP); Ryouji Kayasuga, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 421 days.

(21) Appl. No.: 11/587,557

(22) PCT Filed: Apr. 25, 2005

(86) PCT No.: PCT/JP2005/007767

§ 371 (c)(1),
(2), (4) Date: Oct. 25, 2006

(87) PCT Pub. No.: WO2005/102381

PCT Pub. Date: Nov. 3, 2005

(65) Prior Publication Data

US 2007/0238769 A1   Oct. 11, 2007

(30) Foreign Application Priority Data

Apr. 26, 2004 (JP) ............... 2004-129454

(51) Int. Cl.
A61K 31/70 (2006.01)
A61K 31/425 (2006.01)
(52) U.S. Cl. ........................ 514/12; 514/370
(58) Field of Classification Search ............... 514/12, 514/370

See application file for complete search history.

(56) References Cited

U.S. PATENT DOCUMENTS

2004/0235728 A1* 11/2004 Stoch et al. ............... 514/12

FOREIGN PATENT DOCUMENTS

| WO | WO 03/013518 A1 | 2/2003 |
| WO | WO 03/039534 A1 | 5/2003 |
| WO | WO 03/091202 A1 | 11/2003 |

OTHER PUBLICATIONS

Tatsumoto, Toshio "Kotsusoshosho Chiryo no Genjo to Tenbo", Igaku no Ayumi, 2001, p. 617-620, vol. 198, No. 9.
Stroup, George B. et al., "Potent and selective inhibition of human cathepsin K leads to inhibition of Bone resorption in vivo in a non-human primate", Journal of Bone and Mineral Research, 2001 p. 1739-1746, vol. 16, No. 10.

* cited by examiner

Primary Examiner—Raymond J Henley, III
(74) Attorney, Agent, or Firm—Sughrue Mion, PLLC

(57) ABSTRACT

The present invention relates to an agent for increasing BMD characterized by use of a cathepsin K inhibitor as a bone resorption inhibitor in combination with a type of PTH as a bone formation stimulator. This agent for increasing BMD is useful for the treatment of osteoporosis, bone fracture, arthritis, rheumatoid arthritis, osteoarthritis, hypercalcemia, osteometastasis of carcinoma, periodontal disease, bone Paget's disease and other bone metabolic diseases. For example, as the cathepsin K inhibitor, there can be mentioned a compound of formula (W) and a salt thereof, etc.

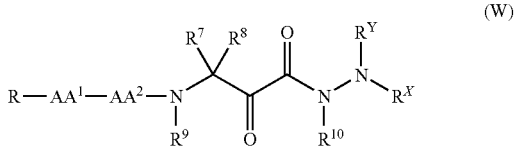

(W)

7 Claims, 5 Drawing Sheets

**; p < 0.01 VS. CONTROL (STUDENT'S t-TEST)

**; p < 0.01 VS. CONTROL (STUDENT'S t-TEST)

BONE DENSIFYING AGENT CHARACTERIZED BY USE OF CATHEPSIN K INHIBITOR WITH PTH

TECHNICAL FIELD

The present invention relates to an agent for increasing bone mineral density (BMD) comprising a cathepsin K inhibitor and a type of parathyroid hormone (PTH) as active ingredients.

More specifically, the present invention relates to a treating and/or preventive agent for bone metabolic diseases comprising a cathepsin K inhibitor and a type of PTH as active ingredients.

BACKGROUND ART

Cathepsin K is a kind of cysteine protease and it belongs to papain superfamily. Cathepsin K is specifically recognized in osteoclast and it has a decomposing activity against bone substrate [J. Biol. Chem., 271, 12517 (1996)], so it is expected that cathepsin K inhibitor shows an effect as a bone resorption inhibitor, against osteoporosis, bone fracture, arthritis, rheumatoid arthritis, osteoarthritis, hypercalcemia, osteometastasis of carcinoma, periodontal disease, bone Paget's disease and other bone-metabolic diseases, in which pathological bone resorption is recognized.

On the other hand, PTH (also called parathyroid hormone or parathormone) is a hormone which is assumed to be produced in the chief cells of parathyroid, and it increases blood calcium concentration and is controlled by the phosphorus level.

It is known that PTH shows a stimulating effect on bone formation by intermittant administration and that it increases BMD. Since PTH has a stimulating effect on bone formation, unlike in the case of existing drugs consisting mainly of bone resorption inhibitors, PTH is expected to be a new type of a drug for osteoporosis.

Osteoporosis is classified in two types of pathologies; primary osteoporosis and secondary osteoporosis. Primary osteoporosis consists mainly of postmenopausal osteoporosis and senile osteoporosis and the like. Secondary osteoporosis consists mainly of diabetic osteoporosis and steroidal osteoporosis and the like.

Both menopausal osteoporosis and senile osteoporosis show the pathologies which is disorder of bone turnover caused by inbalance of bone resorption and bone formation. Therefore, in the treatment of osteoporosis, bone resorption inhibitors and bone formation stimulators are effective and the bone turnover balance may be improved by the combining them effectively.

Examples of bone resorption inhibitors include, bisphosphonates (salts of bisphosphonic acid, abbreviated as BP hereafter), calcium formulations, estrogen receptor modulators, androgen receptor modulator, calcitonin formulations, α-calcitonin gene-related peptide formulations, ipriflavone formulations, anabolic steroid formulations, anti-RANKL (receptor activator of NF-kappa B ligand) antibody and the like; on the other hand, examples of the bone formation stimulators include, types of PTH PTHrP (parathyroid hormone related protein), BMP (bone morphogenetic protein), prostaglandin receptor agonists (EP2 agonists, EP4 agonists and the like), CaR (calcium sensing receptors) antagonist, GSK (glycogen synthase kinase) inhibitors and the like.

Also, for the treatment and/or prevention of bone metabolic diseases, the followings are also used; vitamin D and its derivatives, vitamin K and its derivatives, strontium formulations, HMG-CoA reductase inhibitors, steroidal drugs, caspase-1 inhibitors, prostaglandin receptor antagonists, farnesoid X receptor agonists, progesterone agonists, anti TN-α antibody, anti-IL-6 antibody, female hormone formulations, antiinflammatory drugs, metalloprotease inhibitors, and the like.

Although BP, which is used for the treatment of osteoporosis, has a bone resorption inhibiting effect, it is acknowledged as a problem that it suppresses bone formation (*Osteoporosis Japan*, 7(2), 11-16 (1999), *Bone*, 23(4), 333-342 (1998)).

Since bone metabolic diseases are often chronic diseases, the treatment thereof is often carried out for a long term. Therefore, it has been considered to use several drugs in combination for the improvement of patients' compliance and the therapeutic effect.

For example, an effect on increasing bone mineral density is to be more expected by combination use of bone formation stimulators and bone resorption inhibitors, but it is clinically demonstrated that alendronate sodium hydrate (BP), one of bone resorption inhibitors, does not show an effect in combination with PTH (a bone formation stimulator) (see *The New England Journal of Medicine*, 349, 13, 1207-1215 (2003); *The New England Journal of Medicine*, 349, 13, 1216-1226 (2003)).

On the other hand, cathepsin K inhibitors are known as the drugs which have a bone resorption inhibiting effect. Cathepsin K inhibitors, unlike BP, do not inhibit simian bone formation (see *Journal of Bone and Mineral Research*, 16, 10, 1739-1746 (2001)).

The mechanism of bone metabolic diseases is poorly understood and it is not fully revealed which combination is best for clinically.

As to the treatment of osteoporosis, it is disclosed that a composition comprising a cathepsin K inhibitor and other agents (BP, an estrogen receptor modulator, an androgen receptor modulator, PTH, PTHrP, an osteoclast proton-ATPase inhibitor, an HMG-CoA reductase inhibitor, an $\alpha_v\beta_3$ receptor antagonist, a p38 kinase inhibitor, growth hormone, an $EP_2$ agonist, a TNF-α inhibitor, a P2X7 receptor agonist, a matrix metalloproteinase inhibitor, a VEGF inhibitor and the like) is useful for the diseases of osteoporosis, osteoarthritis, osteometastasis of carcinoma (see WO03/039534).

On the other hand, it is disclosed that a compound of formula (W)

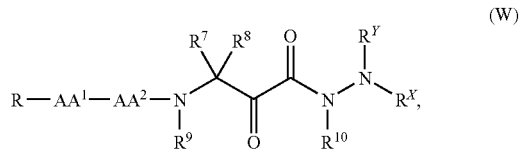

wherein all symbols have the same meaning as described in the specification of WO03/091202, has an inhibitory activity against cathepsin K and that it is useful for the treatment and/or prevention of bone diseases (see WO03/091202).

However, in these literatures, there is no evidence nor implication what kind of effect would be given by actually using a cathepsin K inhibitor and PTH in combination.

DISCLOSURE OF THE INVENTION

In the treatment of bone metabolic diseases such as osteoporosis and the like, a preferable combination of the drugs for the treatment has been hoped for.

Means of Solving the Problems

As a result of energetic studies considering the above circumstances, the present inventors have found that use of a cathepsin K inhibitor (a bone resorption inhibitor), especially the compound of formula (W) as described hereafter, in combination with a type of PTH, especially human PTH (1-34) (a bone formation stimulator), surprisingly, shows more excellent effect in increasing BMD than use of BP (bisphosphonate) (also a bone resorption inhibitor) in combination with PTH, and as a result, these combination is by far more excellent, finally to complete the present invention.

That is, the present invention relates to an agent for increasing BMD comprising a cathepsin K inhibitor and one or more PTH(s).

More specifically, the present invention relates to a treating and/or preventing agent of osteoporosis, bone fracture, arthritis, rheumatoid arthritis, osteoarthritis, hypercalcemia, osteometastasis of carcinoma, periodontal disease, bone Paget's disease and other bone metabolic diseases, comprising a cathepsin K inhibitor and one or more PTH(s).

Much more specifically, the present invention relates to,

[1] an agent for increasing bone mineral density (BMD), comprising a cathepsin K inhibitor and a type of PTH,

[2] the agent for increasing BMD according to the above [1], which is an agent for treating and/or preventing a bone metabolic disease,

[3] the agent for increasing BMD according to the above [1], wherein the cathepsin K inhibitor is a compound of formula (W)

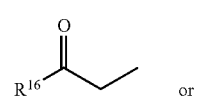

(W)

wherein R is (1) hydrogen atom, (2) CycA, (3) C1-8 alkyl which may be substituted with 1 to 5 of substituent(s) selected from halogen, CycA, nitro, trifluoromethyl and cyano,

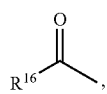

(4)

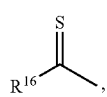

(5)

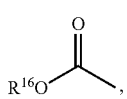

(6)

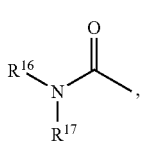

(7)

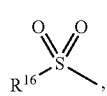

(8)

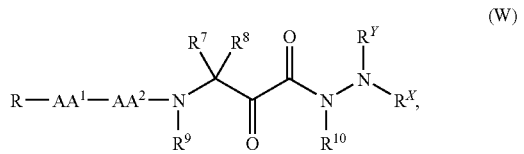

wherein CycA is a C3-15 mono-, bi- or tri-cyclic carbocyclic ring, or a 3- to 15-membered mono-, bi- or tri-cyclic heterocyclic ring comprising 1 to 4 of nitrogen atom(s), 1 to 2 of oxygen atom(s) and/or 1 to 2 of sulfur atom(s), $R^{16}$ is (1) C1-8 alkyl, (2) C2-8 alkenyl, (3) C2-8 alkynyl, (4) CycA, or (5) C1-8 alkyl, C2-8 alkenyl, or C2-8 alkynyl substituted with 1 to 5 of group(s) selected from halogen, nitro, trifluoromethyl, cyano, CycA, —$NR^{18}R^{19}$, —$OR^{18}$, —$SR^{18}$, —NHC(O)— CycA and —NHC(O)O—(C1-8 alkyl), $R^{17}$, $R^{18}$ and $R^{19}$ are each independently, hydrogen atom, C1-4 alkyl, CycA or C1-4 alkyl substituted with CycA, $AA^1$ is (1) a bond, or

(2)

wherein $R^1$ and $R^2$ are each independently, (i) hydrogen atom, (ii) C1-8 alkyl, (iii) CycA, or (iv) C1-8 alkyl substituted with 1 to 5 of group(s) selected from the following (a) to (j):

(a) —$NR^{21}R^{22}$, (b) —$OR^{23}$, (c) —$SR^{23}$, (d) —$COR^{24}$, (e) —$NR^{25}C(O)NR^{21}R^{22}$, (f) guanidino, (g) amidino, (h) CycA, and (j) —$NR^{25}SO_2R^{21}$, or $R^1$ and $R^2$ are taken together to form, C2-8 alkylene (in which one carbon atom in the alkylene may be replaced by oxygen atom, sulfur atom or —$NR^{20}$—, and the alkylene may be substituted with —$NR^{21}R^{22}$, —$OR^{23}$ or oxo), wherein $R^{20}$ is hydrogen atom, C1-4 alkyl, —C(O)O(C1-4 alkyl), CycA, or C1-4 alkyl substituted with CycA, $R^{21}$, $R^{22}$, $R^{23}$ and $R^{25}$ are each independently, hydrogen atom, C1-4 alkyl, CycA, or C1-4 alkyl substituted with CycA, $R^{24}$ is C1-4 alkyl, CycA, —$NR^{21}R^{22}$, —$OR^{23}$, —$SR^{23}$, or C1-4 alkyl substituted with CycA, $R^3$ is hydrogen atom, C1-8 alkyl, CycA, or C1-8 alkyl substituted with CycA, or $R^3$ is taken together with $R^1$ to form C2-6 alkylene (in which one carbon atom in the alkylene may be replaced by oxygen atom, sulfur atom or —$NR^{20}$—, and the alkylene may be substituted with —$NR^{21}R^{22}$, —$OR^{23}$, —$SR^{23}$ or oxo), or R and $AA^1$ may be taken together to form

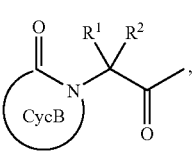

wherein CycB is a 5- to 12-membered mono- or bi-cyclic heterocyclic ring and the other symbols have the same meanings as hereinbefore, $AA^2$ is (1) a bond,

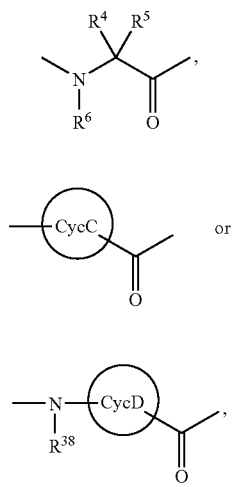

wherein $R^4$ and $R^5$ are each independently, (i) hydrogen atom, (ii) C1-8 alkyl, (iii) CycA or (iv) C1-8 alkyl substituted with 1 to 5 of group(s) selected from the following (a) to (j):

(a) $-NR^{31}R^{32}$, (b) $-OR^{33}$, (c) $-SR^{33}$, (d) $-COR^{34}$, (e) $-NR^{35}C(O)NR^{31}R^{32}$, (f) guanidino, (g) amidino, (h) CycA and (j) $-NR^{35}SO_2R^{31}$, or $R^4$ and $R^5$ may be taken together to form C2-8 alkylene (one carbon atom in the alkylene chain may be replaced by oxygen atom, sulfur atom or $-NR^{30}-$, and the alkylene may be substituted with $-NR^{31}R^{32}$, $-OR^{33}$, $-SR^{33}$, or oxo), wherein $R^{30}$ is hydrogen atom, C1-4 alkyl, $-C(O)O(C1-4$ alkyl), CycA, or C1-4 alkyl substituted with CycA, $R^{31}$, $R^{32}$, $R^{33}$ and $R^{35}$ are each independently, hydrogen atom, C1-4 alkyl, CycA or C1-4 alkyl substituted with CycA, $R^{34}$ is C1-4 alkyl, CycA, $-NR^{31}R^{32}$, $-OR^{33}$, $-SR^{33}$, or C1-4 alkyl substituted with CycA, $R^6$ is hydrogen atom, C1-8 alkyl, CycA, or C1-8 alkyl substituted with CycA, or $R^6$ is taken together with $R^4$ or R to form a C2-6 alkylene (one carbon atom in the alkylene chain may be replaced by oxygen atom, sulfur atom or $-NR^{30}-$, and the alkylene may be replaced by $-NR^{31}R^{32}$, $OR^{33}$, $SR^{33}$, or oxo), $R^{38}$ is hydrogen atom, C1-4 alkyl, CycA, or C1-4 alkyl substituted CycA, or when $AA^1$ is a bond, $R^{38}$ may be taken together with R to form C2-6 alkylene (one carbon atom in the alkylene may be substituted with oxygen atom, sulfur atom or $-NR^{37}-$, wherein $R^{37}$ is hydrogen atom or C1-4 alkyl, CycC is a 3- to 17-membered mono- or bi-cyclic heterocyclic ring, CycD is a C3-14 mono- or bi-cyclic carbocyclic ring or a 3- to 14-membered mono- or bi-cyclic heterocyclic ring, or $AA^2$ may be taken together with $AA^1$ to form

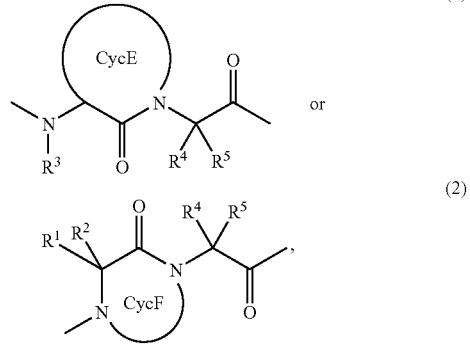

wherein CycE is a 4- to 18-membered mono- or bi-cyclic heterocyclic ring, CycF is a 5- to 8-membered mono-cyclic heterocyclic ring, and the other symbols have the same meanings as described hereinbefore, $R^7$ and $R^8$ are each independently, (1) hydrogen atom, (2) C1-8 alkyl, (3) CycA, or (4) C1-8 alkyl substituted with 1 to 5 of group(s) selected from the following (i) to (x):

(i) $-NR^{41}R^{42}$, (ii) $-OR^{43}$, (iii) $-SR^{43}$, (iv) $-COR^{44}$, (v) $-NR^{45}C(O)NR^{41}R^{42}$, (vi) guanidino, (vii) amidino, (viii) CycA, (ix) $-NR^{45}SO_2R^{41}$ and (x) $-P(O)(OR^{46})(OR^{47})$, or $R^7$ and $R^8$ may be taken together to form C2-8 alkylene (one carbon atom in the alkylene chain may be replaced by oxygen atom, sulfur atom or $-NR^{40}-$, and the alkylene may be substituted with $-NR^{41}OR^{42}$, $-OR^{43}$, $-SR^{43}$ or oxo), $R^{40}$ is hydrogen atom, C1-4 alkyl, $-C(O)O(C1-4$ alkyl), CycA, or C1-4 alkyl substituted with CycA, $R^{41}$, $R^{42}$, $R^{43}$ and $R^{45}$ are each independently, hydrogen atom, C1-4 alkyl, CycA, or C1-4 alkyl substituted with CycA, $R^{44}$ is C1-4 alkyl, CycA, $-NR^{41}R^{42}$, $-OR^{43}$, $-SR^{43}$, or C1-4 alkyl substituted with CycA, $R^{46}$ and $R^{47}$ are each independently, hydrogen atom or C1-8 alkyl, $R^9$ is hydrogen atom, C1-8 alkyl, CycA, or C1-8 alkyl substituted with CycA, or $R^9$ may be taken together with $R^7$ or R to form C2-6 alkylene (one carbon atom in the alkylene chain may be replaced by oxygen atom, sulfur atom or $-NR^{40}-$, and the alkylene may be substituted with $-NR^{41}R^{42}$, $-OR^{43}$, $-SR^{43}$, or oxo, wherein all symbols have the same meanings as described hereinbefore),

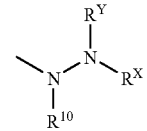

is a group represented by the following (1), (2) or (3):

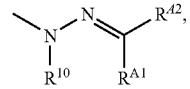

wherein $R^{A1}$ and $R^{A2}$ are each independently, (i) hydrogen atom, (ii) C1-8 alkyl, (iii) C2-8 alkenyl, (iv) $-NR^{Z1}R^{Z2}$, (v)

—OR$^{Z3}$, (vi) —SR$^{Z3}$, (vii) —COR$^{Z4}$, (viii) CycP, (ix) C1-8 alkyl or C2-8 alkenyl substituted with 1 to 5 of group(s) selected from CycP, —NR$^{Z1}$R$^{Z2}$, —OR$^{Z3}$, —SR$^{Z3}$, —COR$^{Z4}$, —SO$_2$R$^{Z4}$, —COOR$^{Z3}$, —CONR$^{Z1}$R$^{Z2}$, —SO$_2$NR$^{Z1}$R$^{Z2}$ and —P(O)(OR$^{Z5}$)(OR$^{Z6}$), wherein R$^{Z1}$ and R$^{Z2}$ are each independently, hydrogen atom, C1-8 alkyl, C2-8 alkenyl, CycP, C2-8 acyl, or C1-8 alkyl substituted with CycP, C2-8 acyl, C1-8 alkoxy, C1-8 alkylthio, mono(C1-8 alkyl)amino or di(C1-8 alkyl)amino, R$^{Z3}$ is hydrogen atom, C1-8 alkyl, C2-8 alkenyl, CycP, or C1-8 alkyl substituted with 1 to 5 of group(s) selected from CycP, C1-8 alkoxy, C1-8 alkylthio, amino, mono(C1-8 alkyl)amino, di(C1-8 alkyl)amino and C2-8 acyl, R$^{Z4}$ is C1-8 alkyl, CycP, or C1-8 alkyl substituted with 1 to 5 of group(s) selected from CycP, C1-8 alkoxy, C1-8 alkylthio, mono(C1-8 alkyl)amino, di(C1-8 alkyl)amino and C2-8 acyl, R$^{Z5}$ and R$^{Z6}$ are each independently, hydrogen atom or C1-8 alkyl, CycP is a C4-10 carbocyclic ring or a 5- to 10-membered heterocyclic ring comprising 1 to 4 of nitrogen atom(s), 1 to 2 of oxygen atom(s) and/or 1 to 2 of sulfur atom(s), and R$^{10}$ has the same meaning as described hereinbefore, or R$^{A1}$ and R$^{A2}$ may be taken together with the adjacent carbon atom to form CycH

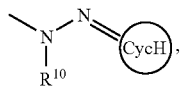

wherein CycH is a C4-10 mono- or bi-cyclic carbocyclic ring or a 4- to 10-membered mono- or bi-cyclic heterocyclic ring and R$^{10}$ has the same meaning as described hereinbefore, R$^{A1}$ and R$^{10}$ may be taken together with the adjacent carbon atom and nitrogen atom to form

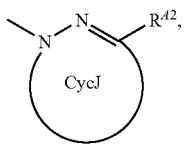

wherein CycJ is a 5- to 10-membered mono- or bi-cyclic heterocyclic ring, R$^{A2}$ has the same meaning as described hereinbefore,

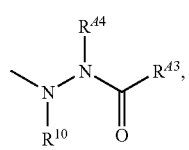

wherein R$^{A3}$ is (i) C1-8 alkyl, (ii) C2-8 alkenyl, (iii) NR$^{Z1}$R$^{Z2}$, (ix) —OR$^{Z3}$, (v) —SR$^{Z3}$, (vi) —COR$^{Z4}$, (vii) CycP, or (viii) C1-8 alkyl or C2-8 alkenyl substituted with 1 to 5 of group(s) selected from —NR$^{Z1}$R$^{Z2}$, —OR$^{Z3}$, —SR$^{Z3}$, —COR$^{Z4}$, —SO$_2$R$^{Z4}$, CycP and —P(O)(OR$^{Z5}$)(OR$^{Z6}$), wherein all symbols have the same meanings as described hereinbefore, R$^{A4}$ is (i) hydrogen atom, (ii) C1-8 alkyl, (iii) C2-8 alkenyl, (iv) —COR$^{Z4}$, (v) CycP, or (vi) C1-8 alkyl, or C2-8 alkenyl substituted with 1 to 5 of group(s) selected from CycP, —NR$^{Z1}$R$^{Z2}$, —OR$^{Z3}$, —SR$^{Z3}$, —COR$^{Z4}$, —SO$_2$R$^{Z4}$, —COOR$^{Z3}$, —CONR$^{Z1}$R$^{Z2}$, —SO$_2$NR$^{Z1}$R$^{Z2}$ and —P(O)(OR$^{Z5}$)(OR$^{Z6}$), wherein all symbols have the same meanings as described hereinbefore, R$^{10}$ has the same meaning as described hereinbefore, or R$^{A3}$ and R$^{A4}$ may be taken together with the adjacent carbon atom and nitrogen atom to form

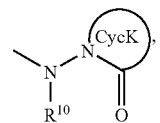

wherein CycK is a 5- to 10-membered mono- or bi-cyclic heterocyclic ring, and R$^{10}$ has the same meaning as described hereinbefore, or R$^{A3}$ and R$^{10}$ may be taken together with the adjacent carbon atom and nitrogen atom to form

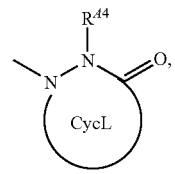

wherein CycL is a 5- to 10-membered mono- or bi-cyclic heterocyclic ring, and R$^{A4}$ has the same meaning as described hereinbefore, (3)

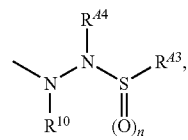

wherein n is an integer of 1 or 2, and the other symbols have the same meanings as described hereinbefore, R$^{A3}$ and R$^{A4}$ may be taken together with the adjacent nitrogen atom and sulfur atom to form

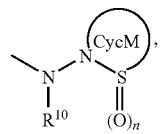

wherein CycM is a 5- to 10-membered mono- or bi-cyclic heterocyclic ring, and the other symbols have the same meaning as described hereinbefore, or R$^{A3}$ and R$^{10}$ may be taken together with the adjacent nitrogen atom and sulfur atom to form

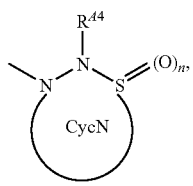

wherein CycN is a 5- to 10-membered mono- or bi-cyclic heterocyclic ring, and the other symbols have the same meanings as described hereinbefore, CycA's, each independently, and CycA, CycB, CycC, CycD, CycE, CycF, CycH, CycJ, CycK, CycL, CycM, CycN and CycP may be each independently substituted with 1 to 5 of $R^{27}$, $R^{27}$ is (1) C1-8 alkyl, (2) halogen, (3) —$NR^{11}R^{12}$, (4) —$OR^{13}$, (5) —$SR^{13}$, (6) CycG, (7) nitro, (8) cyano, (9) oxo, (10) —$COR^4$, (11) —$SO_2R^{14}$, (12) —$P(O)(OR^{15})(OR^{15})$, (13) guanidino, (14) amidino, or (15) C1-8 alkyl substituted with 1 to 5 of group(s) selected from the following (i) to (xii);

(i) halogen, (ii) —$NR^{11}R^{12}$, (iii) —$OR^{13}$, (iv) —$SR^{13}$, (v) CycG, (vi) nitro, (vii) cyano, (viii) —$COR^{14}$, (ix) —$SO_2R^{14}$, (x) —$P(O)(OR^{15})(OR^{15})$, (xi) guanidino, and (xii) amidino, wherein $R^{11}$ and $R^{12}$ are each independently, hydrogen atom, C1-4 alkyl, C1-4 alkoxy, —C(O)O—(C1-4 alkyl), CycG, or C1-4 alkyl substituted with CycG, $R^{13}$ is hydrogen atom, C1-4 alkyl, trifluoromethyl, CycG, or C1-4 alkyl substituted with CycG, CycGs are each independently, a 4- to 10-membered mono- or bi-cyclic carbocyclic ring, or a 5- to 10-membered mono- or bi-cyclic heterocyclic ring comprising 1 to 4 of nitrogen atom(s), 1 to 2 of oxygen atom(s) and/or 1 to 2 of sulfur atom(s), $R^{14}$ is C1-8 alkyl, CycG, —$NR^{11}R^{12}$, —$OR^{13}$, —$SR^{13}$, or C1-8 alkyl substituted with CycG, —$NR^{11}R^{12}$, —$OR^{13}$ or —$SR^{13}$, $R^{15}$s are, each independently, hydrogen atom or C1-8 alkyl, when CycH, CycJ, CycK, CycL, CycM or CycN contains a saturated carbon atom, it may form a spiro ring with CycQ at the saturated carbon atom, wherein CycQ is a C3-10 saturated or partially unsaturated mono-cyclic carbocyclic ring or a 5- to 8-membered saturated or partially unsaturated mono-cyclic heterocyclic ring comprising one of —$NR^Q$—, wherein $R^Q$ is C1-8 alkyl, C2-8 acyl, —$SO_2$—(C1-8 alkyl), benzoyl, benzenesulfonyl, or toluenesulfonyl, one of oxygen atom and/or one of optionally oxidized sulfur atom, a salt thereof, an N-oxide thereof, a solvate thereof or a prodrug thereof,

[4] the agent for increasing BMD according to the above [3], wherein the compound of formula (W) is
(1) N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide,
(2) N-[(1S)-3-{(2Z)-2-[(4R)-3,4-dimethyl-1,3-thiazolidin-2-ylidene]hydrazino}-2,3-dioxo-1-(tetrahydro-2H-pyran-4-yl)propyl]cycloheptanecarboxamide,
(3) N-{(1S)-1-cyclohexyl-3-[(2,5-dioxo-1-pyrrolidinyl)amino]-2,3-dioxopropyl}cycloheptanecarboxamide,
(4) N-((1S)-3-{(2Z)-2-[(4S)-3-ethyl-4-methyl-1,3-thiazolidin-2-ylidene]hydrazino}-2,3-dioxo-1-tetrahydro-2H-pyran-4-ylpropyl)cycloheptanecarboxamide,
(5) N-((1R)-3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide,
(6) N-{3,3-dimethyl-1-[[(2Z)-2-(3-methyl-1,3-thiazolidin-2-ylidene)hydrazino](oxo)acetyl]butyl}cyclohexanecarboxamide,
(7) N-{3-[(2Z)-2-(3-methyl-1,3-thiazolidin-2-ylidene)hydrazino]-2,3-dioxo-1-tetrahydro-2H-pyran-4-ylpropyl}cyclohexanecarboxamide,
(8) N-(3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide or
(9) (N-((1S)-3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxamide),

[5] the agent for increasing BMD according to the above [3], wherein the compound of formula (W) is
N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide or
N-[(1S)-3-{(2Z)-2-[(4R)-3,4-dimethyl-1,3-thiazolidin-2-ylidene]hydrazino}-2,3-dioxo-1-(tetrahydro-2H-pyran-4-yl)propyl]cycloheptanecarboxamide,

[6] the agent for increasing BMD according to the above [1], wherein the cathepsin K inhibitor is orally administered and the type of PTH is parenterally administered,

[7] the agent for increasing BMD according to the above [3], further comprising one or more selected from a prostaglandin receptor agonist, a prostaglandin receptor antagonist, a vitamin D or a derivative thereof, a calcium formulation, a vitamin K and a derivative thereof a calcitonin formulation, a strontium formulation, an estrogen receptor modulator, anti-TNF-α antibody, anti-IL-6 antibody, an HMG-CoA reductase inhibitor, a female hormone formulation, an antiinflammatory drug, PTHrP, a bone formation protein formulation, an androgen receptor modulator, a steroidal drug, a caspase-1 inhibitor, a farnesoid X receptor agonist, a progesteron agonist, anti-RANKL antibody, a metalloprotease inhibitor, a protein assimilation steroidal formulation, a calcium sensing receptor antagonist and a glycogen synthase kinase inhibitor.

[8] the agent for increasing BMD according to the above [2], wherein the bone metabolic disease is osteoporosis, bone fracture, arthritis, rheumatoid arthritis, osteoarthritis, hypercalcemia, osteometastasis of carcinoma, osteosarcoma, periodontal disease and/or bone Paget's disease,

[9] the agent for increasing BMD according to the above [1], wherein the cathepsin K inhibitor is the compound of formula (W) described in the above [3], a salt thereof, an N-oxide thereof, a solvate thereof or a prodrug thereof, and a type of PTH is human PTH (1-34),

[10] the agent for increasing BMD according to the above [9], wherein the compound of formula (W) is
N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide or
N-[(1S)-3-{(2Z)-2-[(4R)-3,4-dimethyl-1,3-thiazolidin-2-ylidene]hydrazino}-2,3-dioxo-1-(tetrahydro-2H-pyran-4-yl)propyl]cycloheptanecarboxamide,

[11] a method for increasing BMD, comprising administering to a mammal an effective amount of the compound of formula (W) described in the above [3], a salt thereof, an N-oxide thereof, a solvate thereof or a prodrug thereof and a type of PTH, and

[12] use of the compound of formula (W) described in the above [3], a salt thereof, an N-oxide thereof, a solvate thereof or a prodrug thereof and a type of PTH, for the manufacture of an agent for increasing BMD.

That is, the present invention relates to an agent for increasing BMD, and such an agent for increasing BMD is useful for the treatment and/or prevention of osteoporosis, bone fracture, arthritis, rheumatoid arthritis, osteoarthritis, hypercalcemia, osteometastasis of carcinoma, osteosarcoma, periodontal disease and/or bone Paget's disease and other bone metabolic diseases.

In the present invention, cathepsin K inhibitors are not limited in particular, if known in general. The examples include, the compounds described in the specifications of WO01/40204, WO01/44214, WO01/55118, WO01/55123, WO02/96892, WO03/91202 and the like.

In the present invention, the cathepsin K inhibitor is preferably a compound described in the specification of WO03/091202, i.e. the compound of formula (W), a salt thereof, an N-oxide thereof, a solvate thereof or a prodrug thereof.

The salts of the compound of formula (W) are pharmaceutically acceptable and low-toxic and water soluble ones are preferable. Examples for appropriate salts include, salts of alkali metals (potassium, sodium, lithium and the like), salts of alkaline earth metals (calcium, magnesium and the like), ammonium salts (tetramethylammonium salt, tetrabutylammonium salt and the like), salts of organic amines (triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine and the like), acid addition salts [salts of inorganic acids (hydrochloride, hydrobromide, hydroiodide, sulfate, phosphate, nitrate and the like), salts of organic acids (acetate, trifluoroacetate, lactate, tartrate, oxalate, fumarate, maleate, benzoate, citrate, methanesulfonate, ethanesulfonate, benzenesulfonate, toluenesulfonate, isethionate, glucronate, gluconate and the like) and the like].

Examples of the N-oxides of the compound of formula (W) include, those compounds wherein a nitrogen atom in the compound of formula (W) is oxidized. The N-oxides of the present invention may be further converted into the above alkali metal salts, alkaline earth metal salts, ammonium salts, organic amine salts, acid addition salts or the like.

Examples of solvates of the compound of formula (W) include, solvates of water, alcohols (ethanol, and the like) and the like. The solvates are preferably non-toxic and water-soluble. Examples of the solvates of the compound of formula (W) include, solvates of the alkali metal salts, alkaline earth metal salts, the ammonium salts, the organic amine salts, the acid addition salts, the N-oxides and the like.

The compound of formula (W) may be converted into the salts as described hereinbefore, N-oxides as described hereinbefore, solvates as described hereinbefore by known methods.

The prodrugs of the compound of formula (W) mean the compounds converted into the compound of formula (W) by the reactions of enzymes, gastric acid and the like in an organism. As the prodrugs of the compound of formula (W), when the compound of formula (W) has amino group, the amino group of the compound is acylated, alkylated, or phosphorylated, (e.g. the amino group of the compound of formula (W) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, tert-butylated and the like); when the compound of formula (W) has hydroxy group, the hydroxy group of the compound is acylated, alkylated, phosphorylated, borated (e.g. the hydroxy group of the compound of formula (W) is acetylated, palmitoylated, propanoylated, pivaloylated, succinylated, fumarylated, alanylated, dimethylaminomethylcarbonylated and the like); when the compound of formula (W) has carboxy group, the carboxy group of the compounds is esterified, amidated (e.g., the carboxy group of the compound of formula (W) is ethylesterified, phenylesterified, carboxymethylesterified, dimethylaminomethylesterified, pivaloyloxymethylesterified, ethoxycarbonyloxyethylesterified, phthalidylesterified, (5-methyl-2-oxo-1,3-dioxolen-4-yl)methylesterified, cyclohexyloxycarbonylethylesterified, methylamidated and the like); and the like. These compounds can be manufactured by the conventional methods. In addition, the prodrugs of the compounds of formula (W) may be solvates or non-solvates. The prodrugs of the compound of formula (W) may be those ones which are converted to a compound of formula (W) in physiological conditions as described in *Molecular Design*, as Vol. 7 of Development of pharmaceutical drugs, 1990. 163-198, Hirokawa Publishing. And the compound of formula (W) may be labeled with isotopes (e.g. $^3H$, $^{14}C$, $^{35}S$, $^{125}I$ and the like) and the like.

As the compound of formula (W), those compounds described in the specification of WO03/091202 are all preferable and more preferably, a compound of formula (W-1)

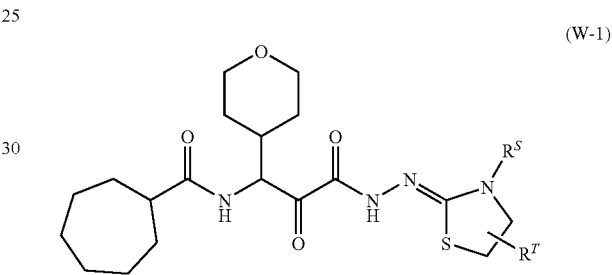

wherein $R^S$ and $R^T$ are each independently, hydrogen atom, C1-4 alkyl such as methyl, ethyl and the like, a compound of formula (W-2)

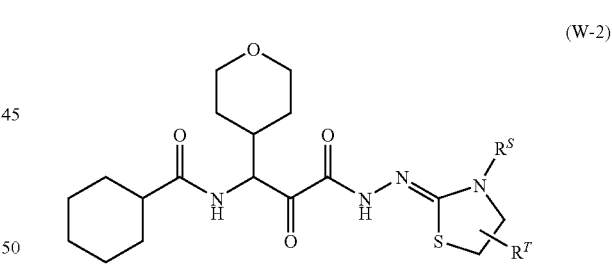

wherein all symbols have the same meanings as described hereinbefore, a compound of formula (W-3)

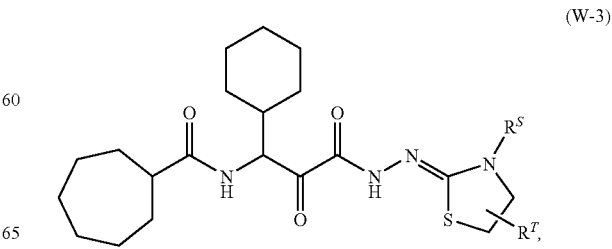

wherein all symbols have the same meanings as described hereinbefore, a compound of formula (W-4)

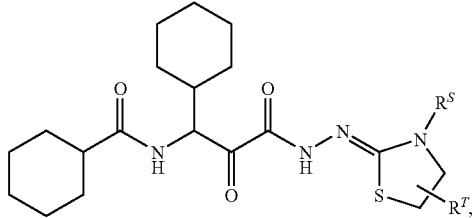
(W-4)

wherein all symbols have the same meanings as described hereinbefore, a compound of formula (W-5)

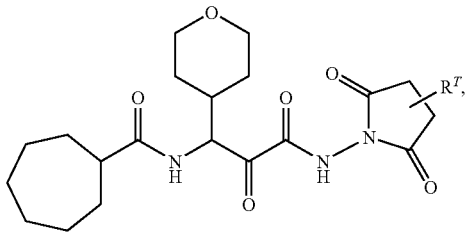
(W-5)

wherein $R^T$ has the same meaning as described hereinbefore, a compound of formula (W-6)

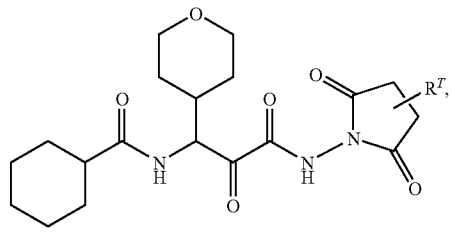
(W-6)

wherein $R^T$ has the same meaning as described hereinbefore, a compound of formula (W-7)

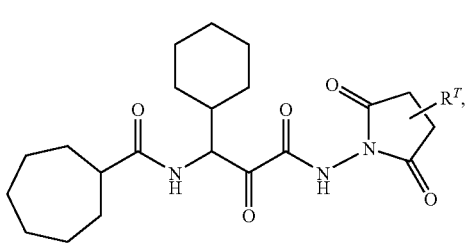
(W-7)

wherein $R^T$ has the same meaning as described hereinbefore, a compound of formula (W-8)

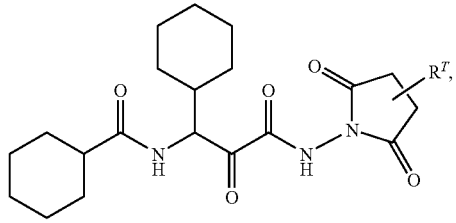
(W-8)

wherein $R^T$ has the same meaning as described hereinbefore, a compound of formula (W-9)

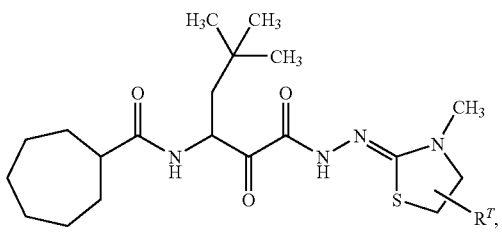
(W-9)

wherein $R^7$ has the same meaning as $R^T$, a compound of formula (W-10)

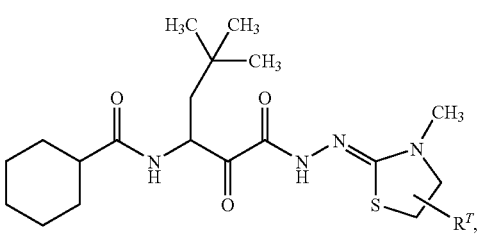
(W-10)

wherein $R^T$ has the same meaning as described hereinbefore, a compound of formula (W-1-1)

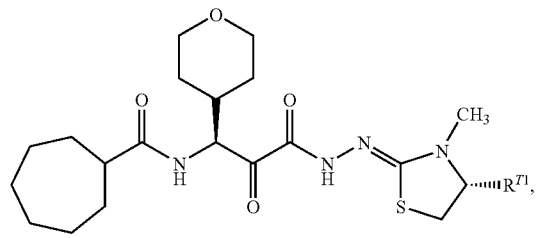
(W-1-1)

wherein $R^{T1}$ is hydrogen atom or methyl, the symbol indicates that the substituent attached thereto is in front of the sheet (β-position), and the symbol indicates that the substituent attached thereto is behind the sheet (α-position)), a salt thereof, an N-oxide thereof, a solvate thereof and a prodrug thereof.

Particularly preferable are, (1) N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide hydrochloride (compound described in the example 8(52) of the specification of WO03/091202, hereafter called the compound (I)), (2) N-[(1S)-3-{(2Z)-2-[(4R)-3,4-dimethyl-1,3-thiazolidin-2-ylidene]hydrazino}-2,3-dioxo-1-(tetrahydro-2H-pyran-4-yl)propyl]cycloheptanecarboxamide (compound described in the example 10(7) of idem), (3) N-{(1S)-1-cyclohexyl-3-[(2,5-dioxo-1-pyrrolidinyl)amino]]-2,3-dioxopropyl}cycloheptanecarboxamide (compound described in the example 5(14) of idem), (4) N-((1S)-3-{(2Z)-2-[(4S)-3-ethyl-4-methyl-1,3-thiazolidin-2-ylidene]hydrazino}-2,3-dioxo-1-tetrahydro-2H-pyran-4-ylpropyl)cycloheptanecarboxamide (compound described in the example 10 of idem), (5) N-((1R)-3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide (compound described in the example 10(62) of idem), (6) N-{3,3-dimethyl-1-[[(2Z)-2-(3-methyl-1,3-thiazolidin-2-ylidene)hydrazino](oxo)acetyl]butyl}cyclohexanecarboxamide hydrochloride (compound described in the examples 8(10) of idem), (7) N-{3-[(2Z)-2-(3-methyl-1,3-thiazolidin-2-ylidene)hydrazino]-2,3-dioxo-1-tetrahydro-2H-pyran-4-ylpropyl}cyclohexanecarboxamide hydrochloride (compound described in the example 8(24) of idem), (8) N-(3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide (compound described in the example 10(2) of idem) and the like.

And, the enantiomer of the compound (5), i.e. (9) (N-((1S)-3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxamide) is also preferably used.

In addition to the compound (1) to (9), corresponding free compounds, salts thereof, solvates thereof or prodrugs thereof are preferable as well.

Particularly preferably, (1) N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide hydrochloride and (2) N-[(1S)-3-{(2Z)-2-[(4R)-3,4-dimethyl-1,3-thiazolidin-2-ylidene]hydrazino}-2,3-dioxo-1 (tetrahydro-2H-pyran-4-yl)propyl]cycloheptanecarboxamide are used.

The compounds of (1) to (8) may be prepared according to the method described in the specification of WO03/091202. The compound of (9) may be prepared by subjecting the compound (8) to recrystallization from isopropylamine and ethyl acetate. Specifically, it may be prepared by the following example 1.

In the present invention, the dosage of the compound of formula (W) which is used as a cathepsin K inhibitor, depends on age, sex, body weight, symptom, race and the like, and it also depends on the condition of the disease, administration route, the condition of the kidneys and liver of the patient, and the compound to be used and the kind of salt. Those skilled in the art can easily subscribe the required dose in order to suppress the progress of the symptoms or to treat the disease.

The compound of formula (W) may be administered orally, intravenously, topically such as subcutaneously or into a joint cavity, or transdermally, and the like. The interval between administrations are, for example, approximately one hour, approximately two hours, approximately 4 hours, approximately 6 hours, approximately 12 hours, approximately 1 day, approximately 2 days, approximately 3 days, approximately 4 days, approximately 1 week, approximately 2 weeks, approximately 1 month, approximately 2 months, approximately 3 months, approximately 4 months, approximately 6 months, approximately 1 year and the like. Once to four times a day dosing may be carried out.

The compound of formula (W) may be used in various kinds of formulations according to known methods per se, e.g. the methods described in the specification of WO03/091202 as a pharmaceutical composition.

Cathepsin K inhibitors may be administered as a solid formulation for oral administration, e.g. tablets, pills, dispersants, granules, capsules and the like.

Capsules include, hard capsules and soft capsules.

In these solid agents for oral administration, one active substance or more may be administered as they are, or may be admixed with diluting agents (lactose, mannitol, glucose, microcrystalline cellulose, starch and the like), binding agents (hydroxypropylcellulose, polyvinylpyrrolidone, magnesium aluminometasilicate and the like), disintegrating agents (cellulose calcium glycolate and the like), lubricating agents (magnesium stearate and the like), stabilizing agents, dissolution assisting agents (glutamic acid, aspartic acid and the like) and the like, to be formulated by the conventional methods. And also, if required, they may be coated with one or more of coating agent (white sugar, gelatin, hydroxypropylcellulose, hydroxypropylmethylcellulose phthalate and the like). The solid agents also include capsules made of absorbable substances such as gelatin.

Examples for liquid formulations for oral administration include, for example, a pharmaceutically acceptable aqueous formulation, suspensions, emulsions, syrups, elixirs and the like. In these liquid formulations, one or more of active substance is diluted in generally used diluents (purified water, ethanol or a mixture thereof and the like). And this liquid formulation may further include moistening agents, suspending agents, emulsifying agents, sweetening agents, flavoring agents, aromatic agents, preserving agents, buffering agents and the like.

For example, when the compound of formula (W) is orally administered, as the formulation, each of a tablet, a pill, a dispersant, a granule and a capsule is preferable. Such formulations may include preferably, approximately 1 to 1,000 mg of a cathepsin K inhibitor, more preferably approximately 5 to 300 mg.

In the present invention, examples of the types of PTH include, PTH and PTH analogues.

PTH represents parathyroid hormone (parathormone) and examples of PTH include natural types of PTH, recombinant PTHs manufactured by a genetically engineering method, chemically synthesized PTHs, and preferable examples include, human PTH consisting of 84 amino acid residues (human PTH (1-84)), especially recombinant human PTH (1-84) manufactured by a genetically engineering method. And examples of the PTH derivatives include, for example, a partial peptide of the above-mentioned PTH, a peptide wherein the constitutive amino acid of PTH itself or its partial peptide is replaced by other amino acids or deleted, or added with one or more of amino acid and the like, all of which have an analogous activity as PTH. Examples of the partial peptides of PTH include, human PTH (1-34), human PTH (1-64), human PTH (35-84), bovine PTH (1-34) and the like. PTH (1-34) represents human PTH (human PTH (1-34), human PTH (1-34) amide and the like) consisting of 34 amino acid residue from N-terminus to 34th amino acid, particularly recombinant human PTH (1-34) (e.g. CHS13340, which has been developed as an intranasal formulation) which was manufactured by a genetically engineering method.

One kind of PTH may be solely used or several types of PTH may be used in combination.

Preferable examples of the amino acid replacement include, the replacement of constitutive amino acid at the 8-position by leucine or norleucine, at the 18-position by leucine or norleucine, at the 34-position by tyrosine and the like.

In the present invention, the purity of the type of PTH is not necessarily 100%, but substantially pure types of PTH are also acceptable. {Substantially pure} means that the PTH is purified to show a single peak in the HPLC, and preferably, it means that the PTH is confirmed to be single by the techniques of SDS-PAGE, capillary electrophoresis or the like. Such types of PTH may be prepared or confirmed by the method described in JP6-87897(A), JP4-505259(T), *J. Biol. Chem.*, 265, 17854 (1990), or by the method improved those described in the literature.

Types of PTH are preferably administered parenterally, and more preferably intravenously, by topical injections such as subcutaneous injections or injections in the joint cavity, transdermally, intranasally, and the like, more preferable are subcutaneous injection and intranasal administration. Types of PTH are preferably administered intermittently. Intermittent administration is carried out at the interval of, for example, approximately 1 hour, approximately 2 hours, approximately 4 hours, approximately 6 hours, approximately 12 hours, approximately 1 day, approximately 2 days, approximately 3 days, approximately 4 days, approximately 1 week, approximately 2 weeks, approximately 1 month, approximately 2 months, approximately 3 months, approximately 4 months, approximately 6 months, approximately 1 year and the like.

In the present invention, the dosages of types of PTH depend on the diseases, symptom, severity, conditions of the diseases, administration route, conditions of kidneys and liver of the patient, the compound or the salt and the like, but those skilled in the art can prescribe the necessary amount for dosage in order to suppress the progress of symptoms or to treat the disease. In systemical administration, approximately 1 µg to 1000 µg per kg (body weight) is preferable and more preferable is 5 µg to 200 µg per kg (body weight).

In the present invention, the additives used in the pharmaceutical compositions are selected from diluting agents, binding agents, moistening agents, stabilizing agents or the like.

In the present invention, when the cathepsin K inhibitors and/or the types of PTH are used as an injection, they may be dissolved, suspended or emulsified in a medium.

Examples of the medium include, distilled water for injection, physiological saline, vegetable oil, propylene glycol, polyethylene glycol, alcohols such as ethanol and the like and the combination thereof.

And the injections may further include, stabilizing agents such as sodium citrate, sodium edetate and the like; solubilizing agents such as glutamic acid, aspartic acid, polysorbate80® and the like; suspending agents such as surfactants (stearyl triethanolamine, sodium lauryl sulfate, lauryl aminopropionate, lecithin, benzalkonium chloride, benzetonium chloride, glyceryl monostearate, polyoxyethylene hydrogenated castor oil, polysorbate, and the like), polyvalent alcohol (glycerin, macrogol and the like), saccharides (sorbitol, mannitol, sucrose, and the like), celluloses (methyl cellulose, carboxymethyl cellulose, hydroxypropylmethyl cellulose and the like), hydrophilic macromolecules (polyvinylalcohol, polyvinylpyrrolidone, carboxyvinyl polymer, sodium carboxymethyl cellulose, methyl cellulose, chondroitin sulfate and the like), emulsifying agents such as glycerin esters, saponin (sophora saponin, quillai extract, soybean saponin, and the like), sucrose fatty acid ester (sucrose ester and the like), lecithin (vegetable lecithin, egg-york lecithin, soybean lecithin, and the like), and the like; soothing agents such as benzylalcohol, chlorobutanol, propyleneglycol, ethyl aminobenzoate, lidocaine and the like), buffering agents such as phosphates (sodium hydrogen phosphate, sodium dihydrogen phosphate and the like), boric acid, borax, acetate (sodium acetate and the like), carbonates (sodium carbonate, calcium carbonate, potassium carbonate and the like), citric acid, L-glutamate sodium and the like; pH adjusters such as sodium hydroxide, potassium hydroxide, trisodium phosphate, sodium dihydrogen phosphate, hydrochloric acid, nitric acid, citric acid, boric acid, acetic acid and the like; preserving agents such as parahydroxybenzoic acid esters (propyl parahydroxybenzoate, butyl parahydroxybenzoate and the like), parabens (methylparaben, ethylparaben, propylparaben, butylparaben and the like), cationic soap (benzalkonium chloride, benzethonium chloride, chlorhexidine gluconate, cetylpyridium chloride, and the like), alcohol derivatives (chlorobutanol, benzylalcohol, phenethylalcohol, and the like), organic acid and a salt thereof (sodium dehydroacetate, sorbic acid, sodium sorbate, and the like), phenols (parachloromethoxyphenol, parachlorometacresol, and the like); tonicity agents such as glucose, D-sorbitol, sodium chloride, glycerin, D-mannitol, potassium chloride, concentrated glycerin, propyleneglycol, sucrose and the like; and the like. These are sterilized in the final scheme or are prepared by asepticism. Sterile solid compositions, such as freeze-dried composition, may be prepared, to sterilize or to solve in sterile distilled water for injection or other sterile solvents before use.

In the present invention, cathepsin K inhibitors or types of PTH may be provided, as well as oral formulations or injective formulations which are prepared by normal method for manufacture, for example, in such formulations as microencapsulation or entrapment in a gel-like sheet, for the purpose of localization or slow-action. In the formulating process, pharmaceutically acceptable additives may be added. And for the purpose of extending the serum half-life, a formulation modified by polyethylene glycol and the like is also acceptable. Preferable are non-invasive formulations.

As these additives, for example, a base component, a stabilizer, a preserving agent, an emulsifying agent, a coloring agent, an aromatic agent, a soothing agent, a binding agent, a buffering agent and the like, and specifically, for example, calcium carbonate, lactose, sucrose, sorbit, mannitol, starch, amylopectin, cellulose derivatives, gelatin, cacao butter, distilled water for injection, an aqueous solution of sodium chloride, Ringer's solution, glucose solution, human serum albumin and the like.

When the pharmaceutical formulations are prepared in the present invention using these additives, the additives may be selected and used as described in Pharmaceutical Additives Inventory (Published by Medical Jurisprudence Committee of The Pharmaceutical Manufacturer's Association of Tokyo and Medical Jurisprudence Research Committee of Osaka Pharmaceutical Manufacturer's Association). And the amount of the additives varies depending on the dosage forms and the like if only they are pharmaceutically acceptable.

In the present invention, types of PTH may be administered either topically or systemically, and particularly, when it is administered aiming a particular bone, topical administration is excellent. For topical administration, intermittent administration is desirable.

In the present invention, types of PTH may be absorbed from an adhesive formulation.

By contriving ways to administration route, it is possible to administer types of PTH without invasion, and therefore, in the present invention, they may be administered parenterally. Examples of parenteral administration include, subcutaneous administration, intravenous administration, intranasal administration, pulmonary administration and the like.

By use of a cathepsin K inhibitor in combination with a type of PTH, an additive effect on bone densification is recognized, compared with sole administration of a type of PTH. Preferable administration schedule include, the way in which a cathepsin K inhibitor is administered orally every day and a type of PTH is intermittently administered. Also, when cathepsin K inhibitor is solely administered for a certain period (e.g. approximately one week, approximately one month, approximately two months, approximately three months, approximately 6 months, approximately one year and the like), followed by combination administration with PTH. And also preferable embodiment is, that at first types of PTH are solely administered for a certain period, and then types of PTH are administered in combination with a cathepsin K inhibitor. And to start dosing of a cathepsin K inhibitor and a type of PTH is also preferable.

In addition to a cathepsin K inhibitor and a type of PTH, those agents which are generally used in the treatment and/or prevention of bone metabolic diseases, for example, a calcium formulation (e.g. calcium lactate, precipitated calcium carbonate, and the like), an estrogen receptor modulator (e.g. toremifene citrate, tamoxifen citrate, raloxifene hydrochloride, lasofoxifene tartrate, bazedoxifene acetate, PSK-3471 and the like), an androgen receptor modulator, a calcitonin formulation (e.g. salmon calcitonin (STH-32, SMC20-51), chicken calcitonin (MCI-536), secalciferol, elcatonin, TJN-135 and the like), α-calcitonin gene-related peptide formulation, ipriflavone formulations (e.g. ipriflavone and the like), an anabolic steroid formulation (nandrolone decanoate, nandrolone phenylpropionate, nandrolone cyclohexylpropionate, metenolone enanthate, mestanolone, stanozolol, oxymetholone and the like), anti-RANKL (receptor activator of NF-kappa B ligand) antibody (e.g. AMG162 and the like), PTHrP (parathyroid hormone related protein) (e.g. RS-66271, hPTHrP, and the like), BMP (bone morphogenetic protein) (e.g. YM484(BMP-2) and the like), a prostaglandin receptor agonist (e.g. $EP_4$ agonist (e.g. ONO-4819 and the like), $EP_2$ agonists (e.g. ONO-8815 and the like), nitroflurbiprofen and the like), a CaR (calcium sensing receptor) antagonist, a GSK (glycogen synthase kinase) inhibitor, vitamin D (e.g. vitamin $D_2$ (ergocalciferol), vitamin $D_3$ (cholecalciferol), and the like) and their derivatives (e.g. alphacalcidol, falecalcitriol, calcitriol, 1α,25-dihydroxycholecarciferol, dihydrotachysterol, ST-630, KDR, ST-630, ED-71, rocaltrol (Ro44-7190) and the like), vitamin K (e.g. vitamin $K_1$ (phytonadione), vitamin $K_2$ (menatetrenone) and the like) and their derivatives, a strontium formulation (e.g. strontium ranelate and the like), an HMG-CoA reductase inhibitor (e.g. pravastatin, simvastatin, pitavastatin, lovastatin, rosuvastatin, atorvastatin, fluvastatin, cerivastatin and the like), a steroidal agent (e.g. KB-889 (OD14, Tibolone), Hipros (TZP-4238) and the like), a caspase-1 inhibitor (e.g. pralnacasan, nitroflurbiprofen and the like), a prostaglandin receptor antagonist, a farnesoid X receptor agonist (e.g. SR-45023A and the like), a progesterone agonist (e.g. trimegestone and the like), an anti TNF-α antibody (e.g. infliximab, etanercept and the like), an anti IL-6 antibody (e.g. MRA and the like), a female hormone formulation, an antiinflammatory drug, a metalloprotease inhibitor (e.g. minocycline hydrochloride and the like) and the like.

Toxicity:

The compound of the present invention is very low and it is safe enough for medical use.

Effect of the Invention:

By use of a cathepsin K inhibitor in combination with a type of PTH, BMD is increased more efficiently than use of a type of PTH solely. Such combination use is useful for the prevention and/or treatment of osteoporosis, bone fracture, arthritis, rheumatoid arthritis, osteoarthritis, hypercalcemia, osteometastasis of carcinoma, osteosarcoma, periodontal disease, bone Paget's disease and other bone metabolic diseases. For example, by administering a cathepsin K inhibitor orally and administering a type of PTH parenterally (subcutaneous injection, intranasal administration, and the like) the BMD of the patients suffering from bone metabolic diseases such as osteoporosis is increased efficiently.

BEST MODE FOR CARRYING OUT THE INVENTION

Figure 1:
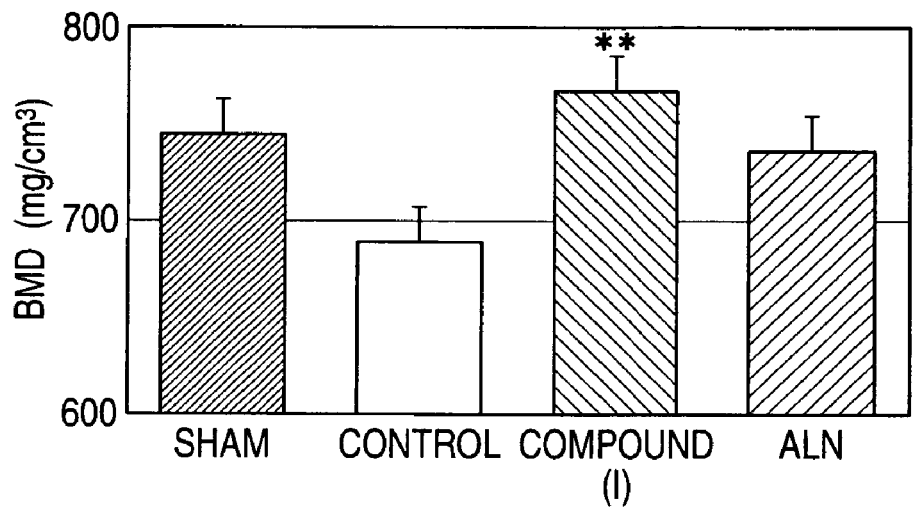
FIG. 1 represents the BMD of the left leg tibia (4 mm slice from proximal end) when an intermediate autopsy was performed in experiment 1 (administration schedule 1).

The following examples illustrate the present invention, but the present invention is not limited to them. The solvents shown in the parentheses of chromatography separation and TLC show the eluting or developing solvents and the ratios are by the volume. The solvent shown in the parentheses of NMR shows the solvent used in the measurement.

In the present specification, the compounds were named by a computer program which carries out a nomenclature according to IUPAC rules generally, i.e. ACD/Name (registered trademark, Advanced Chemistry Development Inc.) or ACD/Name Batch (registered trademark, Advanced Chemistry Development Inc.), or named according to IUPAC nomenclature.

EXAMPLE 1

Preparation of (N-((1S)-3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxamide) (compound (9))

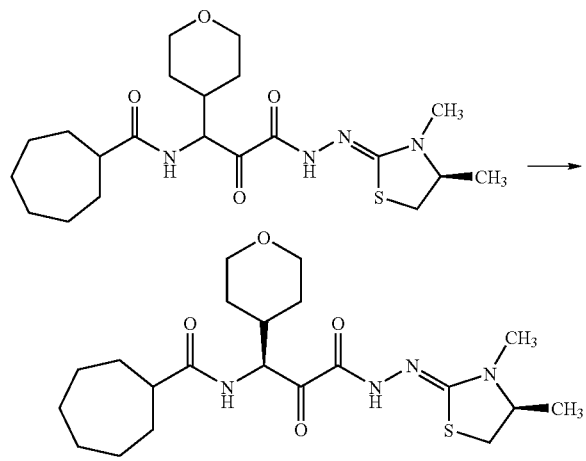

Compound (8); (N-(3-{(2Z)-2-[(4R)-3,4-dimethyl-1,3-thiazolidin-2-ylidene]hydrazino]-2,3-dioxo-1-tetrahydro-2H-pyran-4-ylpropyl)cycloheptanecarboxamide) (1.97 g) was recrystallized from isopropanol/ethyl acetate (1/1 by volume). From this mother liquor, the mixture of L-isomer (N-((1S)-3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxamide) and D-isomer (N-((1R)-3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxamide, whose D/L ratio was 32/68 (1.15 g, pale yellow powder) was obtained.

This washed with ethyl acetate, and it was allowed to stand toward room temperature, and the crystals were collected by filtration. The mother liquor was concentrated and the residue washed with ethyl acetate, and it was allowed to stand toward room temperature. The crystals were collected by filtration to give a compound wherein the D/L ratio was 16/84 (270 mg, pale yellow powder).

This was recrystallized from ethyl acetate to give the title compound (43 mg, white needle crystal) having the following physical data.

TLC:Rf 0.40 (methylene chloride:methanol=9:1); NMR (CDCl$_3$): δ 1.33 (d, J=6.22 Hz, 3H), 1.33 (m, 16H), 2.36 (m, 2H), 2.88 (dd, J=10.80, 6.04 Hz, 1H), 2.98 (s, 3H), 3.36 (m, 3H), 3.85 (m, 1H), 3.95 (m, 2H), 5.15 (dd, J=9.15, 6.41 Hz, 1H), 6.45 (d, J=9.15 Hz, 1H), 8.72 (s, 1H).

Biological Examples

The effect of a cathepsin K inhibitor in combination with a type of PTH was confirmed by the following experiments.

For the purpose of clarifying the characteristics, the effect of a cathepsin K inhibitor (a bone resorption inhibitor) in combination with a type of PTH (a bone formation stimulator) was examined using an ovariectomized rat osteoporosis model (abbreviated as OVX hereafter). The effect of a bisphosphonate (BP) in combination with a type of PTH was also examined. The effects were compared with each other.

The compound (I) used as a cathepsin K inhibitor was described in the example 8(52) of the specification of WO03/91202 and it can be prepared according to the method described in the specification.

Alendronate sodium hydrate (abbreviated as ALN hereafter), which was used as a bisphosphonate (BP) was given by LKT laboratories, Inc.

As a type of PTH, human PTH (1-34) amide (APC (Lot.N05129A1); 840 µg/vial), which is a partial peptide of PTH, was used.

<Method>

1) Preparation of the Solutions of the Test Compounds
(1) a solution of the compound (I): The compound (I) was dissolved in 0.5% aqueous solution of methyl cellulose (MC) to give a 0.6 mg/mL solution.
(2) a solution of ALN: ALN was dissolved in a 0.01 mol/L aqueous solution of sodium hydroxide to give a 5.6 mg/mL solution (approximately pH 7), and the solution was diluted with 0.5% MC aqueous solution by 28 times, giving a 0.2 mg/mL solution.
(3) PTH (1-34) solution: PTH (1-34) was dissolved in a saline (10 ml) containing 0.1% bovine serum albumin (BSA) to give a 84 µg/mL solution, and at the time of use it was diluted to the required concentration (2 µg/mL) with a saline containing 0.1% BSA. In the following examples, PTH (1-34) is abbreviated as PTH unless specified.

2) Test Method

Experiment 1 (Administration Schedule 1): Administration in Combination with PTH After Repeated Administration of Bone Resorption Inhibitor Female retired rats (F344/NSlc) were used. At the age of 6 months, 87 rats were assigned to OVX (ovariectomy) and the other 10 rats were assigned to sham operation.

Another 15 rats were assigned to OVX and 5 rats were assigned to sham operation, in order to these groups to an autopsy in the course.

To the 87 rats assigned to OVX, the drugs were administered according to the grouping shown in the following table 1. To the group the compound was administered; a bone resorption inhibitor was administered orally from the next day of OVX over a period of 83 days.

The compound (I), used as a cathepsin K inhibitor, was orally administered twice a day at a dose of 3 mg/kg, and ALN, used as a BP, was orally administered once a day at a dose of 1 mg/kg. On 55 days after OVX, the autopsy was done in autopsy group. Other groups to which the compound was administered, a bone resorption inhibitor was administered orally, and PTH or vehicle (saline containing 0.1% BSA) was administered subcutaneously, 55 days after OVX. When ALN was administered as a bone resorption inhibitor, ALN was orally administered in the first administration, and a vehicle (0.5% MC aqueous solution) was orally administered in the second each day. The interval between the first and the second administration was 5-7 hours.

PTH was administered by subcutaneous injection from the back three times a week by a dose of 10 µg/kg from the 57th day after OVX. The drugs were administed according to the grouping of table 1.

In the group in which the compound was administered, on the 83rd day after OVX, BMD of tibia, lumbar BMD, concentration of urinary C-terminal telopeptide of type I collagen (CTX) and serum osteocalcin (OC) were measured. In the autopsy groups, concentration of urinary CTX and serum OC were measured on samples from the 55th day.

TABLE 1

| | No. | operation | pre-administration of a bone resorption inhibitor | number of examples | administration of PTH (1-34) |
|---|---|---|---|---|---|
| the groups in which the compound was administered | 1 | sham | — | 10 | x |
| | 2 | OVX | — | 10 | x (control) |
| | 3 | OVX | — | 9 | 10 µg |
| | 4 | OVX | compound (I) | 10 | x |
| | 5 | OVX | ALN | 10 | x |
| | 6 | OVX | compound (I) | 9 | 10 µg |
| | 7 | OVX | ALN | 10 | 10 µg |
| autopsy groups | 8 | sham | — | 5 | |
| | 9 | OVX | — | 5 | |
| | 10 | OVX | compound (I) | 5 | |
| | 11 | OVX | ALN | 5 | |

Experiment 2 (Administration Schedule 2) Long Term Administration of Bone Resorption Inhibitor in Combination with a PTH Female retired rats (F344/NSlc) were used. At the age of 6 months, 59 rats were assigned to OVX and the other 10 rats were assigned to sham operation. To the 59 rats assigned to OVX, the drugs were administered according to the grouping shown in the following table 2.

To groups the compound was administered; a bone resorption inhibitor (the compound (I) (3 mg/kg, twice a day orally) as a cathepsin K inhibitor or ALN (1 mg/kg, once a day orally) as a BP) and PTH (1-34) (3 µg/kg, three times a day subcutaneously) were administered for 83 days from the next day of OVX. In the groups to which PTH was not administered, a vehicle (saline containing 0.1% BSA) subcutaneously instead. When ALN was administered as a bone resorption inhibitor, ALN was administered in the first administration and a vehicle (0.5% MC aqueous solution) was orally administered in the second administration each day. The interval between the first and the second administration was 5-7 hours.

of urinary CTX concentration (ng/mg CRE) was displayed by the CTX (ng/mL) that divided by urinary creatinine concentration (mg/mL) on the same individual.

(3) The Method for the Measurement of Serum Osteocalsin (OC) Concentration

Fifty-five days after administration, in the autopsy, collected serum was used to measure the serum OC concentration with a kit for OC measurement (BIOTRAK; Osteocalcin, rat ELISA system).

<Statistical Processing>

In order to compare the sham group and the OVX control group, t-test (EXSAS (version 6.1), ARM SYSTEX CO., LTD.); in order to compare the effectiveness of the test compounds, Tukey test (EXSAS (version 6.1), ARM SYSTEX CO., LTD.), were used respectively. Less than 5% was assumed to be a significant difference.

<Result>

The results are shown in FIGS. 1 to 6.

Experiment 1 (Administration Schedule 1)

TABLE 2

| | No. | operation | pre-administration of a bone resorption inhibitor | number of examples | administration of PTH (1-34) |
|---|---|---|---|---|---|
| the groups in which the compound was administered | 1 | sham | — | 10 | x |
| | 2 | OVX | — | 10 | x (control) |
| | 3 | OVX | — | 10 | 3 µg |
| | 4 | OVX | compound (I) | 9 | x |
| | 5 | OVX | ALN | 10 | x |
| | 6 | OVX | compound (I) | 10 | 3 µg |
| | 7 | OVX | ALN | 10 | 3 µg |

<The Methods for the Measurement of Each Parameter>

(1) The Method for the Measurement of BMD

The BMD was determined by measurement device of peripheral BMD (pQCT: peripheral Quantitative Computed Tomography, XCT-Research SA+Stratec Medizintechnik GmbH, version 5.40) with voxel size 0.12 mm. The BMD of the left proximal tibia (at a point 4 mm from the proximal end) was measured.

(2) The Method for the Measurement of Urinary CTX Concentration

Urine was collected before the day of an autopsy, and urinary CTX was measured with a kit for rat CTX measurement (RatLaps ELISA; nordicbioscience). In measurement of absorbance, microplate reader (SPECTRA MAX 250, Japan Molecular Devices Inc.) was used. The measured value In order to confirm the effect of the compound (I) and ALN, 56 days after OVX, an intermediate autopsy was performed. In FIG. 1, both compounds showed an increasing effect of BMD in the tibia.

Figure 2:
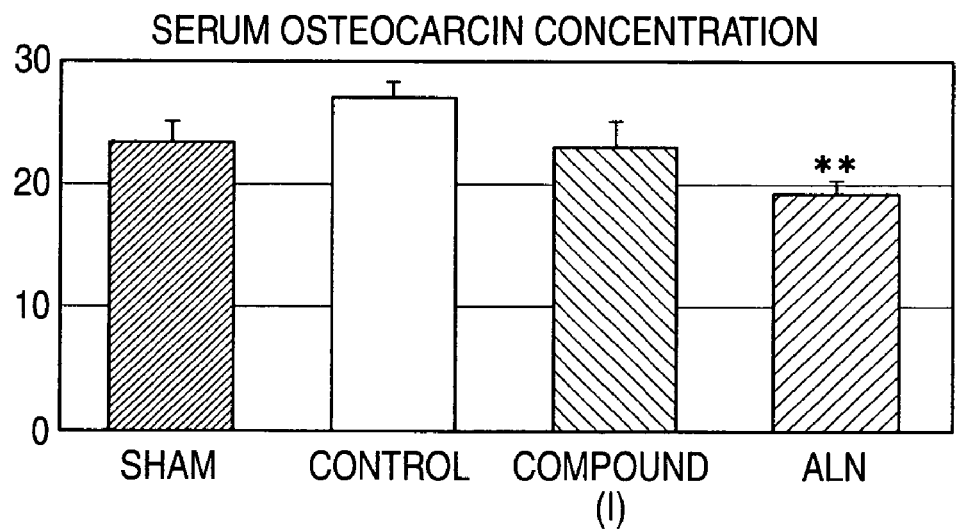
FIG. 2 represents an osteocalcin concentration, which is a bone formation marker, when an intermediate autopsy was performed in experiment 1 (administration schedule 1).

In FIG. 2, a serum OC concentration, bone formation marker, was decreased by the repeated administration of ALN for 55 days. Whereas a serum OC concentration was not decreased by the repeated administration of the compound (I) for 55 days. From these results, although they are both bone resorption inhibitors, a cathepsin K inhibitor does not affect bone formation, and it is obvious that it has a more excellent effect when used in combination with a type of PTH, compared with use of BP in combination with a type of PTH.

Figure 3:
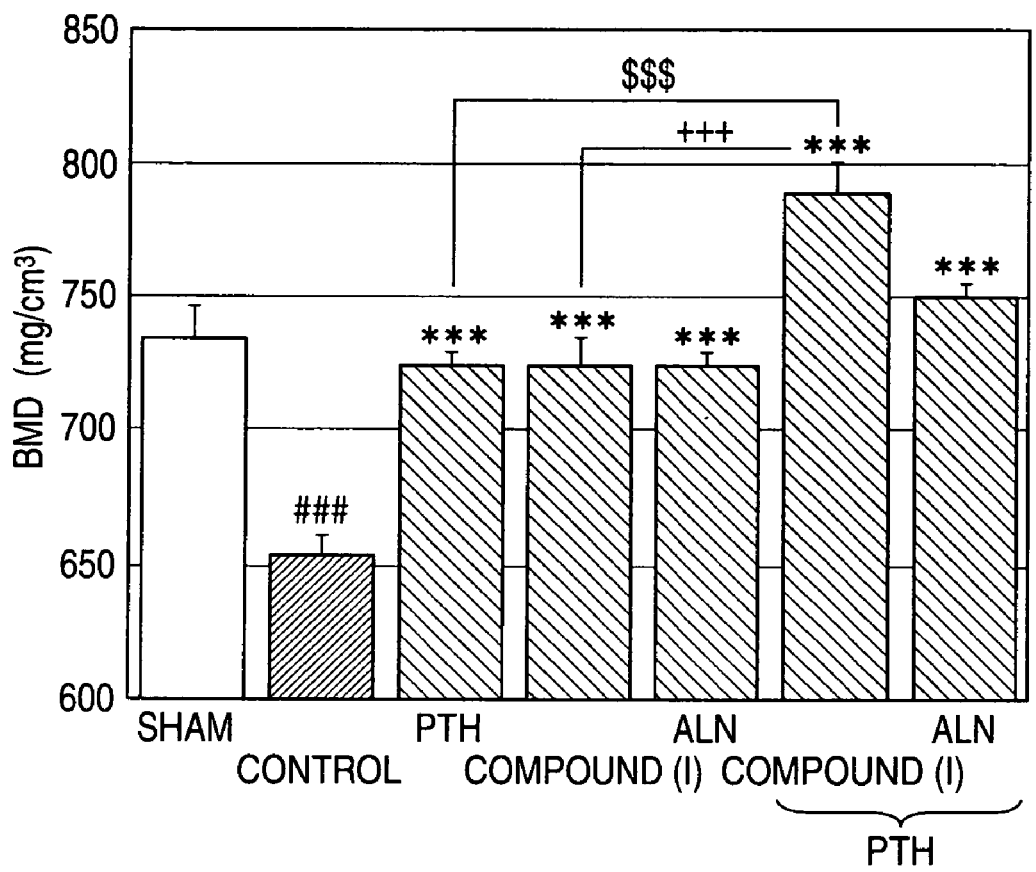
FIG. 3 represents a BMD of the left leg tibia (4 mm slice from proximal end) on the 83rd day in the experiment 1 (administration schedule 1).

FIG. 3 shows that PTH, compound (I) and ALN suppressed the OVX-induced BMD loss in the tibia each alone. The group in which combination with the PTH and compound (I)

showed a significant effect over PTH administration alone. While the compound (I) showed an additive effect in BMD of tibia when used in combination with PTH, ALN did not show any additive effect in combination with PTH.

Figure 4:
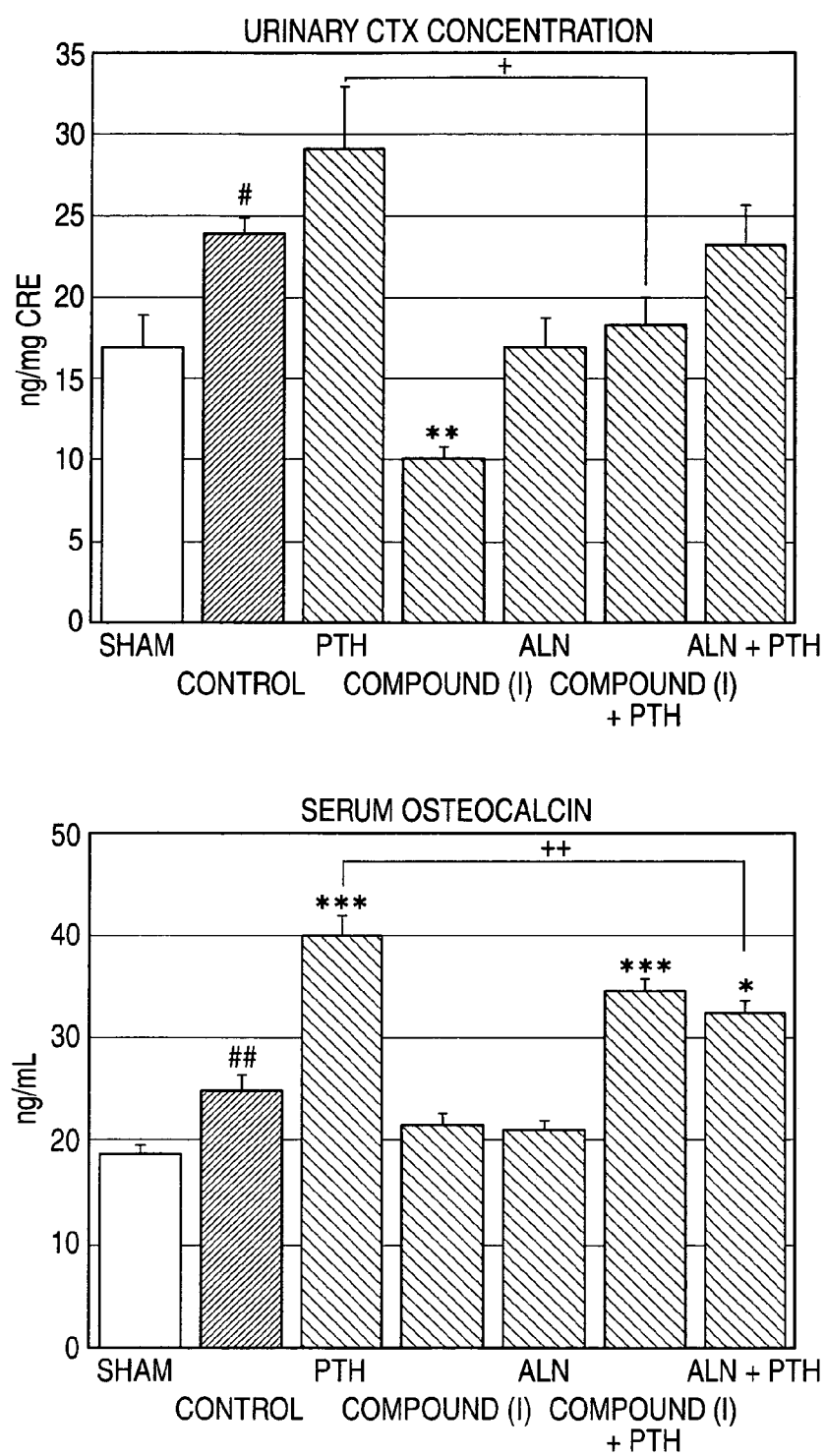
FIG. 4 represents a concentration of bone metabolism marker (urinary CTX concentration, serum osteocalcin concentration) on the 83rd day in the experiment 1 (administration schedule 1).

FIG. 4 shows that the compound (I) showed an inhibitory effect on-urinary CTX concentration both in sole administration and in combination administration with PTH. While ALN showed a urinary CTX inhibitory effect both in sole administration and in combination administration with PTH, the inhibitory effect was weaker than that of compound (I).

FIG. 4 refers to a bone formation marker. The compound (I) did not decrease the serum OC concentration significantly by use in combination with PTH, over PTH sole administration. On the other hand, ALN significantly decreased serum OC concentration which was increased by PTH. Therefore, it was confirmed that cathepsin K inhibitors, unlike ALN, do not show an inhibitory effect on bone formation effect of PTH.

Experiment 2 (Administration Schedule 2)

A bone resorption inhibitor and PTH were administered in combination for a long term.

Figure 5:
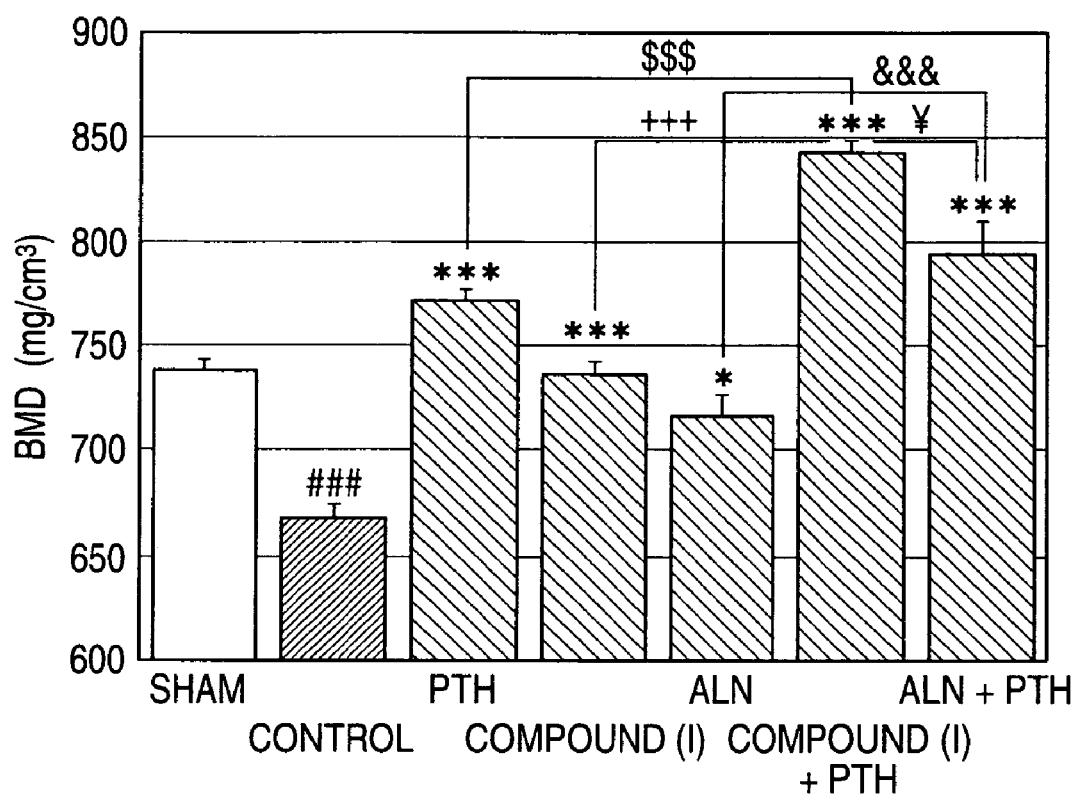
FIG. 5 represents BMD of the tibia (4 mm slice from proximal end) on the 83rd day in the experiment 2 (administration schedule 2).

FIG. 5 shows that PTH, the compound (I) and ALN each inhibited the reduction of BMD of tibia caused by OVX. The effect on increase of BMD of tibia of compound (I) in combination with PTH was greater than that of ALN in combination with PTH.

Figure 6:
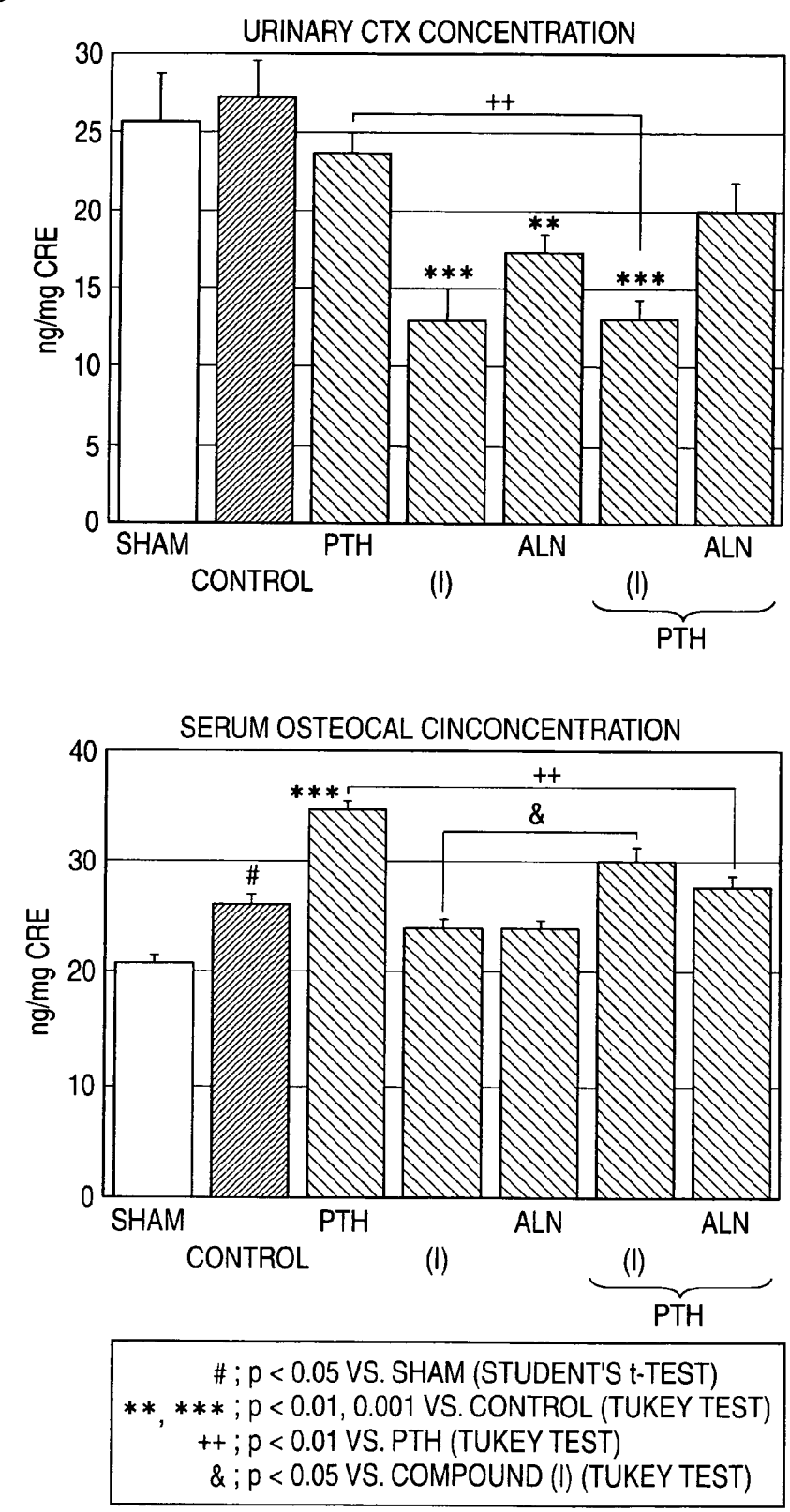
FIG. 6 represents a bone metabolism marker on the 83rd day in the experiment 2 (administration schedule 2) (urinary CTX concentration, serum osteocarcin concentration).

FIG. 6 shows that, the compound (I) has an inhibitory effect on urinary CTX concentration (bone resorption marker) both in sole administration group and in combination administration. However, an inhibitory effect of ALN on urinary CTX was weaker than that of compound (I).

<Discussion>

As to the increase of BMD, as a result of investigation into the effect of two types of bone resorption inhibitors (a cathepsin K inhibitor and a BP) each having different activity, about use in combination with a type of PTH (a bone formation stimulator), combination of cathepsin K inhibitor and a type of PTH had an excellent effect in increase of BMD, over use of BP in combination with a type of PTH.

Particularly, when the bone resorption inhibitor was pre-administered continually for two months, and afterwards, a bone resorption inhibitor was used in combination with a type of PTH (experiment 1), the difference between them proved significant. This is considered to be because pretreatment by BP decreased bone formation and then the effect of PTH was made to be hard to be expressed.

It was demonstrated from the experimental fact that cathepsin K inhibitor does not inhibit bone formation but selectively inhibits bone resorption, however, BP inhibits both of them. Therefore, cathepsin K inhibitors have an excellent effect when used in combination with PTH.

As a bone resorption inhibitor, BP does not have an excellent effect when used in combination with types of PTH, the present inventors have found out that a cathepsin K inhibitor, which is also a bone resorption inhibitor, has an excellent effect when used in combination with types of PTH, compared with BP.

Formulation Example 1

Preparation of a Formulation Comprising 10 mg of a Cathepsin K Inhibitor

The following components were admixed in a conventional method and punched out to give 10,000 tablets each containing 10 mg of the active ingredient.

N-{3-[(2Z)-2-(3-methyl-1,3-thiazolidin-2-ylidene)hydrazino]-2,3-dioxo-1-tetrahydro-2H-pyran-4-ylpropyl}cycloheptanecarboxamide hydrochloride (100 g)
carboxymethylcellulose calcium (disintegrating agent) (20.0 g)
magnesium stearate (lubricant) (10.0 g)
microcrystalline cellulose (870 g)

Formulation Example 2

Preparation of a Formulation Comprising 50 mg of PTH (1-34)

The following components were admixed in a conventional method, and thus given solution was sterilized by a conventional method. To each vial was poured 5 ml of the solution to give 100 vials each containing 50 mg of the active ingredient.

PTH (1-34) (5.0 g)
D-mannitol (5.0 g)
distilled water (60 mL in total)

INDUSTRIAL APPLICABILITY

By use of a cathepsin K inhibitor in combination with a type of PTH, it is possible to be increased BMD more effectively, compared with use of a type of PTH solely, therefore, such combination use is useful for the prevention and/or treatment of osteoporosis, bone fracture, arthritis, rheumatoid arthritis, osteoarthritis, hypercalcemia, osteometastasis of carcinoma, osteosarcoma, periodontal disease, bone Paget's disease and other bone metabolic diseases.

The invention claimed is:

1. A method for increasing bone mineral density, comprising administering to a mammal an effective amount of an agent comprising a cathepsin K inhibitor and a type of PTH, wherein the cathepsin K inhibitor is a compound of formula (W-1):

$$R-AA^1-AA^2-N(R^9)-C(R^7)(R^8)-C(O)-N(R^{10})-N(R^Y)(R^X) \quad (W)$$

wherein $R^S$ and $R^T$ are each independently a hydrogen atom or a C1-4 alkyl group, a salt thereof, an N-oxide thereof, a solvate thereof or a prodrug thereof; and wherein the type of PTH is human PTH (1-34).

2. The method according to claim 1, wherein the agent is an agent for treating a bone metabolic disease.

3. The method according to claim 1, wherein the compound of formula (W-1) is
(1) N-{3-[(2Z)-2-(3-methyl-1,3-thiazolidin-2-ylidene) hydrazine]-2,3-dioxo-1-tetrahydro-2H-pyran-4-ylpropyl} cycloheptanecarboxamide,
(2) N-[(1S)-3-{(2Z)-2-[(4R)-3,4-dimethyl-1,3-thiazolidin-2-ylidene]hydrazino}-2,3-dioxo-1-(tetrahydro-2H-pyran-4-yl)propyl]cycloheptanecarboxamide,
(3) N-((1S)-3-{(2Z)-2-[(4S)-3-ethyl-4-methyl-1,3-thiazolidin-2-ylidene]hydrazino}-2,3-dioxo-1-tetrahydro-2H-pyran-4-ylpropyl)cycloheptanecarboxalflide, (4) N-((1R)-3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptaneCarboxamide,
(5) N-(3-{(2Z)-2-[(4R)-3,4-dimethyl-1,3-thiazolidin-2-ylidene]hydrazino}-2,3-dioxo-1-tetrahydro-2H-pyran-4-ylpropyl)cycloheptanecarboxamide or
(6) (N-((1S)-3-{(2Z)-2-[(4S)-3,4-dimethyl-1,3-thiazolidin-2-ylidene]hydrazino}-2,3-dioxo-1-tetrahydro-2H-pyran-4-ylpropyl)cycloheptanecarboxalmde).

4. The method according to claim 3, wherein the compound of formula (W-1) is

N-{3-[(2Z)-2-(3-methyl-1,3-thiazolidin-2-ylidene)hydrazine]-2,3-dioxo-1-tetrahydro-2H-pyran-4-ylpropyl}cycloheptanecarboxamide or N-[(1S)-3-{(2Z)-2-[(4R)-3,4-dimethyl-1,3-thiazolidin-2-ylidene]hydrazino}-2,3-dioxo-1-(tetrahydro-2H-pyran-4-yl)propyl]cycloheptanecarboxamide.

5. The method according to claim 1, wherein the compound of formula (W-1) is orally administered and the human PTH (1-34) is parenterally administered.

6. The method according to claim 1, wherein the agent further comprises one or more selected from a prostaglandin receptor agonist, a prostaglandin receptor antagonist, an ergocalciferol, a cholecalciferol, an alphacalcidol, a falecalcitriol, a calcitriol, a 1α,25-dihydroxycholecarciferol, a dihydrotachysterol, a ST-630, a KDR, a ST-630, an ED-71, a rocaltrol, a calcium formulation, a phyonadione, a menatetrenone, a calcitonin formulation, a strontium formulation, an estrogen receptor modulator, anti-TNF-α antibody, anti-IL-6 antibody, an HMG-CoA reductase inhibitor, a female hormone formulation, an antiinflammatory drug, PTHrP, a bone formation protein formulation, an androgen receptor modulator, a steroidal drug, a caspase-1 inhibitor, a farnesoid X receptor agonist, a progesteron agonist, anti-RANKL antibody, a metalloprotease inhibitor, a protein assimilation steroidal formulation, a calcium sensing receptor antagonist and a glycogen synthase kinase inhibitor.

7. The method according to claim 2, wherein the bone metabolic disease is osteoporosis, bone fracture, arthritis, rheumatoid arthritis, osteoarthritis, hypercalcemia, osteometastasis of carcinoma, osteosarcoma, periodontal disease and/or bone Paget's disease.

* * * * *

UNITED STATES PATENT AND TRADEMARK OFFICE
CERTIFICATE OF CORRECTION

PATENT NO.        : 7,632,813 B2
APPLICATION NO.   : 11/587557
DATED             : December 15, 2009
INVENTOR(S)       : Yasuo Ochi et al.

It is certified that error appears in the above-identified patent and that said Letters Patent is hereby corrected as shown below:

Please correct claim 1 to read as follows:

1. (currently amended): A method for increasing bone mineral density, comprising administering to a mammal an effective amount of an agent comprising a cathepsin K inhibitor and a type of PTH, wherein the cathepsin K inhibitor is a compound of formula (W-1):

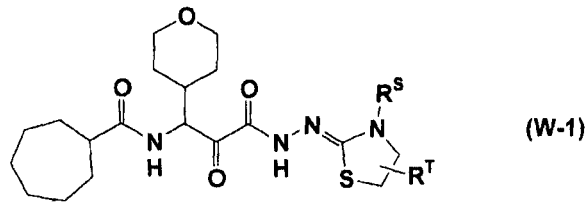

wherein $R^S$ and $R^T$ are each independently a hydrogen atom or a C1-4 alkyl group, a salt thereof, an N-oxide thereof, a solvate thereof or a prodrug thereof; and wherein the type of PTH is human PTH (1-34).

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,632,813 B2  Page 1 of 1
APPLICATION NO. : 11/587557
DATED : December 15, 2009
INVENTOR(S) : Yasuo Ochi et al.

It is certified that error appears in the above-identified patent and that said Letters Patent is hereby corrected as shown below:

Column 26, lines 36-54,

Please correct claim 1 to read as follows:

1. (currently amended): A method for increasing bone mineral density, comprising administering to a mammal an effective amount of an agent comprising a cathepsin K inhibitor and a type of PTH, wherein the cathepsin K inhibitor is a compound of formula (W-l):

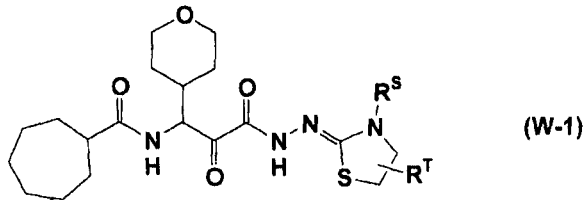

wherein $R^S$ and $R^T$ are each independently a hydrogen atom or a C1-4 alkyl group, a salt thereof, an N-oxide thereof, a solvate thereof or a prodrug thereof; and wherein the type of PTH is human PTH (1-34).

This certificate supersedes the Certificate of Correction issued May 18, 2010.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO.        : 7,632,813 B2
APPLICATION NO.   : 11/587557
DATED             : December 15, 2009
INVENTOR(S)       : Yasuo Ochi et al.

It is certified that error appears in the above-identified patent and that said Letters Patent is hereby corrected as shown below:

Title page, item (*) Notice: should read as follows:

Subject to any disclaimer, the term of this patent is extended or adjusted under 35 U.S.C. 154(b) by 472 days.

Signed and Sealed this

Sixth Day of July, 2010

David J. Kappos
*Director of the United States Patent and Trademark Office*